United States Patent [19]
Allen et al.

[11] Patent Number: 5,467,786
[45] Date of Patent: * Nov. 21, 1995

[54] METHOD FOR REPARING TEARS AND INCISIONS IN SOFT TISSUE

[75] Inventors: William C. Allen, Division of Orthopaedic Surgery, University of Missouri-Columbia, Health Sciences Center, Columbia, Mo. 65212; Michael G. Maurizi, Columbia, Mo.

[73] Assignee: William C. Allen, Columbia, Mo.

[ * ] Notice: The portion of the term of this patent subsequent to Jun. 14, 2011, has been disclaimed.

[21] Appl. No.: 242,788

[22] Filed: May 16, 1994

Related U.S. Application Data

[63] Continuation-in-part of Ser. No. 988,454, Dec. 10, 1992, Pat. No. 5,320,633.

[51] Int. Cl.⁶ ........................... A61B 17/00
[52] U.S. Cl. ........................... 128/898; 606/144
[58] Field of Search ............... 606/144, 232, 606/228, 72, 74, 75; 128/898

[56] References Cited

U.S. PATENT DOCUMENTS

| | | |
|---|---|---|
| 4,006,747 | 2/1977 | Kroenenthal et al. . |
| 4,586,502 | 5/1986 | Bedi et al. . |
| 4,669,473 | 6/1987 | Richards et al. . |
| 4,741,330 | 5/1988 | Hayhurst ............ 606/144 |
| 4,872,451 | 10/1989 | Moore et al. ............ 606/72 |
| 5,085,661 | 2/1992 | Moss ............ 606/139 |
| 5,320,633 | 6/1994 | Allen et al. ............ 606/144 |

*Primary Examiner*—Tamara L. Graysay
*Attorney, Agent, or Firm*—Senniger, Powers, Leavitt & Roedel

[57] ABSTRACT

A method for closing an opening in soft tissue inside the body includes the step of making an incision in the body for permitting access to the interior of the body generally adjacent to the location of the opening in the soft tissue inside the body. An instrument is inserted through the incision to the vicinity of the opening in the soft tissue, and passes through the soft tissue and across the opening in the tissue generally from the first side of the opening to a second side of the opening opposite the first side. At least a part of the instrument lies in a passage in the soft tissue. A first leg of a generally H-shaped suture is pushed generally lengthwise in the instrument into the passage with the first leg and a cross member connecting the first leg to a second leg being resiliently deflected from their relaxed positions relative to one another. The first leg moves back to its relaxed position relative to the cross member upon passing out of the instrument, and extends transversely with respect to the lengthwise extension of the passage across the exit thereof so that the first leg cannot move back into the passage. The second leg extends generally transversely with respect to the lengthwise extension of the passage across the entrance thereof so that the second leg cannot move into the passage. The cross member is disposed in the passage and is sized so that the legs of the suture compress the opening shut. In another aspect, a method for repairing a tear formed by separation of the soft tissue from the bone in which a suture is inserted through the bone and tissue, and across the tear.

7 Claims, 6 Drawing Sheets

METHOD FOR REPARING TEARS AND INCISIONS IN SOFT TISSUE

This application is a continuation-in-part of U.S. application Ser. No. 07/988,454, filed Dec. 10, 1992 now U.S. Pat. No. 5,320,633.

SUMMARY OF THE INVENTION

This invention relates generally to a method for repairing tears and incisions in soft tissue inside the body.

Endoscopic surgery has reduced the need in many cases for more invasive surgical procedures, and permits in nearly all of those cases a quicker recovery from surgery for the patient. Many surgical procedures require suturing of an opening in soft tissue at some point in the procedure. The opening in the soft tissue may be formed intentionally by incision during the course of the procedure, or the opening may be a tear in the soft tissue which necessitated the surgery. Closure of such openings by conventional suturing methods is difficult in endoscopic surgery and may present certain risks. The difficulty arises in endoscopic surgery because of the limited work space for the surgeon.

Endoscopy is commonly employed in the repair of damage to soft tissue in the joints, and in particular the knee. Where joints are concerned, the procedure is generally referred to as arthroscopic surgery. Injury to the knee involving a tear in the meniscus is a common occurrence, often in the context of athletic events, and is prevalent in the younger population. The meniscus is recognized as being vital to the biomechanical stability and protection of the knee joint. Damage to the meniscus can greatly increase the likelihood of the articular surfaces of the knee joint developing conditions such as osteoarthritis. Thus, in many instances it is desirable to repair the torn meniscus with the objective being to prevent instability of the knee joint and to prevent onset of conditions such as osteoarthritis.

Current methods for repairing tears in the meniscus during arthroscopic surgery are very technically challenging for the surgeon and present certain risks during the operation. These techniques require that a long needle with a suture be passed through the torn meniscus and the knee joint. The procedure, in which the needle must pass back and forth through the meniscus and knee joint, increases the risk of damage to the neurovascular structure about the knee. In addition, infectious or fistulous tracks may develop along the lines of suture placement into the knee joint. Many surgeons are dissuaded from attempting such a difficult procedure. In fact, the most common treatment for tears in the meniscus is to remove some or all of the meniscus. This treatment cannot result in the restoration of biomechanical stability of the knee joint or prevent the onset of conditions such as osteoarthritis.

Among the several objects and features of the present invention may be noted the provision of a method for repairing openings in soft tissue inside the body which requires limited surgical invasion of the body; the provision of such a method by endoscopy which is less complex than existing methods; the provision of such a method which reduces trauma to the soft tissue; the provision of such a method by which soft tissue may be reattached to the bone; and the provision of such a method which can be carried out from one side of the opening.

Generally, a method carried out according to the principles of the present invention for closing an opening in soft tissue inside the body includes the step of making an incision in the body for permitting access to the interior of the body generally adjacent to the location of the opening in the soft tissue inside the body. An instrument is inserted through the incision to the vicinity of the opening in the soft tissue inside the body, and passes through the soft tissue and across the opening in the tissue generally from a first side of the opening to a second side of the opening opposite the first side. A portion of the instrument lies in a passage having an entrance on the first side of the opening and an exit on the second side of the opening. A suture means is delivered in the instrument to the passage. The suture means comprises a first leg, a second leg spaced from the first leg and a cross member extending generally transversely with respect to the lengthwise extension of the first and second legs and connecting the first and second legs. The first leg and cross member are pushed generally lengthwise into the passage through the entrance thereof with the first leg and the cross member being resiliently deflected from their relaxed positions relative to one another. The first leg moves back to its relaxed position relative to the cross member upon passing out of the passage through the exit thereof and leaving the instrument, the first leg thereafter extending transversely with respect to the lengthwise extension of the passage across the exit thereof so that the first leg cannot move back into the passage through the exit. The second leg extends generally transversely with respect to the lengthwise extension of the passage across the entrance thereof so that the second leg cannot move into the passage through the entrance. The cross member is disposed in the passage and has a length less than the length of the passage such that the suture means compresses the soft tissue to at least partially close the opening.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Referring now to the drawings a system for closing an opening in soft tissue such as a tear T in a meniscus M at a knee joint includes a tack (FIG. 1D, broadly "suture means") indicated generally at 20, an instrument for delivering the tack to the torn meniscus indicated generally at 22 (FIG. 1C), a push rod (FIG. 1B, broadly "pusher means") indicated generally at 24, and a guide pin indicated generally at 26

Figure 1A:
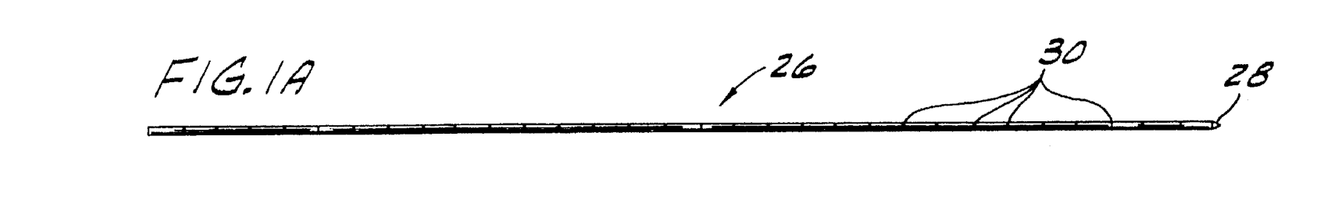
FIG. 1A is a plan of a guide pin of a system for repairing a tear to the meniscus.
Figure 2:
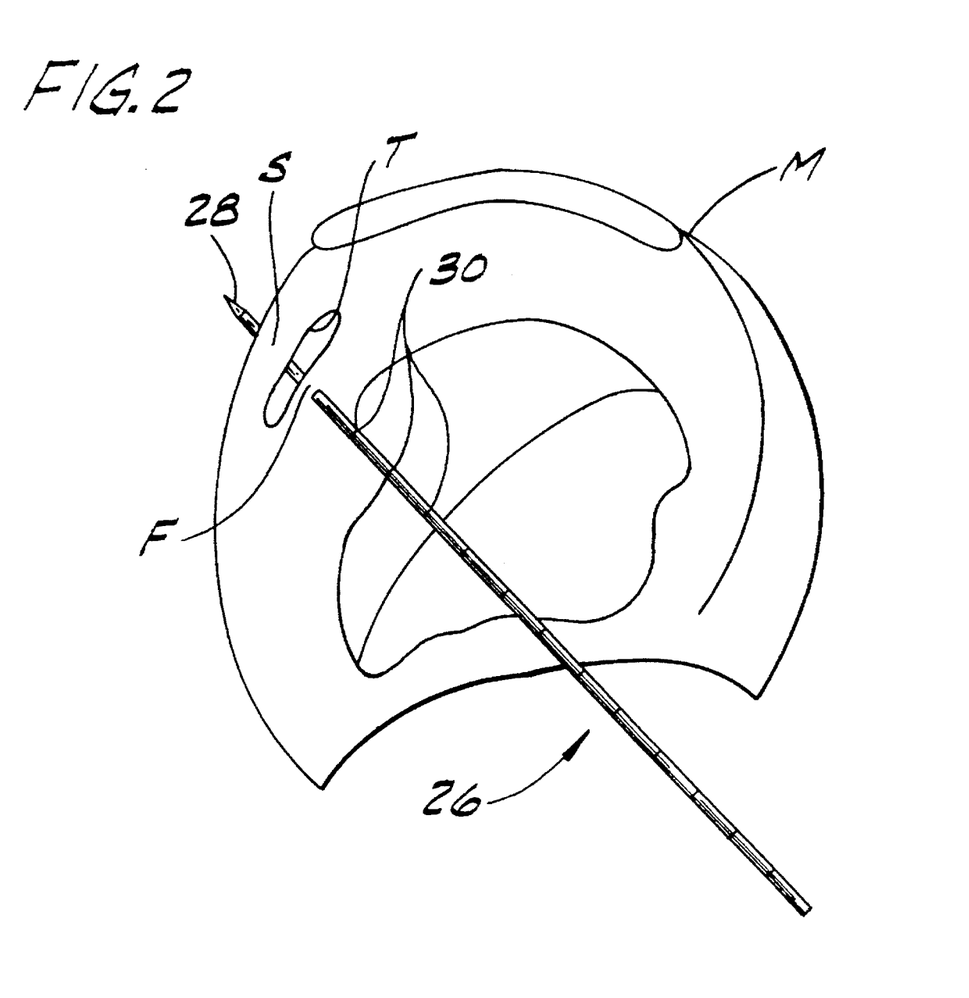
FIGS. 2–5 are schematic views showing the use of the system to repair the torn meniscus.

(FIG. 1A). The guide pin 26, which is preferably made of stainless steel, has a sharpened end 28 for piercing the meniscus M and a plurality of graduations 30 along its length for use in determining the appropriate size of tack 20 to use for closing the tear (FIG. 2). The instrument 22, push rod 24 and guide pin 26 comprise the system for repairing an opening in soft tissue. The use of the guide pin 26 and other components of the system will be described more fully below.

Figure 1B:
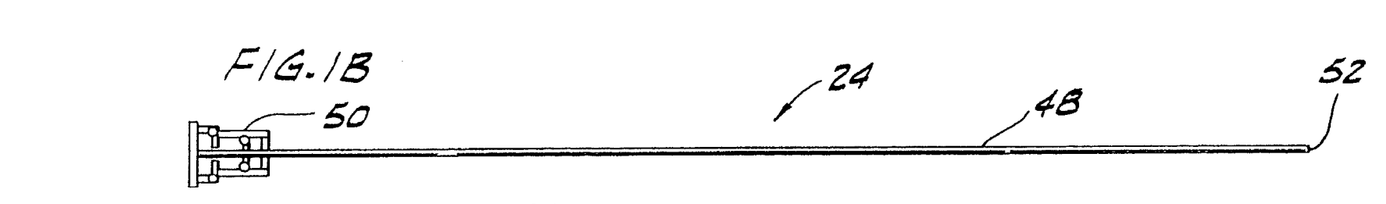
FIG. 1B is a plan of a push rod of the system.
Figure 1C:
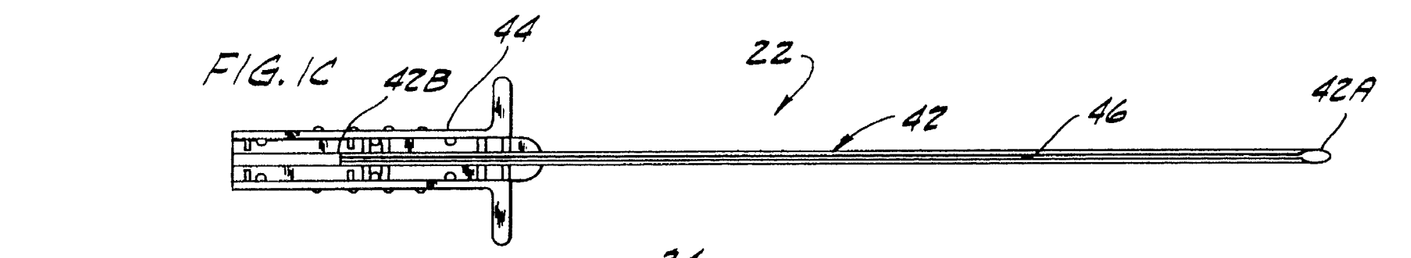
FIG. 1C is a plan of an instrument for delivering a suture to the tear in the meniscus.
Figure 1D:
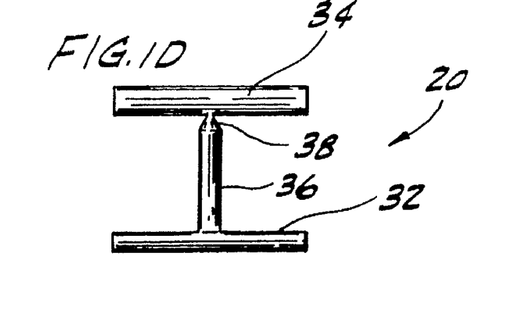
FIG. 1D is a greatly enlarged elevation of a suture tack of the system.

The tack 20 is generally H-shaped, having a first leg 32, a second leg 34 spaced from the first leg and a cross member indicated in its entirety by the reference numeral 36. The cross member 36 extends generally transversely with respect to the lengthwise extensions of the first and second legs 32, 34, and connects the first and second legs. The first and second legs 32, 34, and cross member 36 are generally cylindrical in shape with uniform diameters along their lengths, except the cross member has a tapered section 38 at its end connected to the second leg. The tack 20 is preferably made of an absorbable material of the type well known in the art, such as polyglycolic acid or polydioxane, which will be gradually absorbed by the body after it is used to suture the tear T. Thus, after approximation of the meniscus tissue, it is not necessary to surgically reenter the knee joint to remove the tack 20.

Figures 6, 6A:
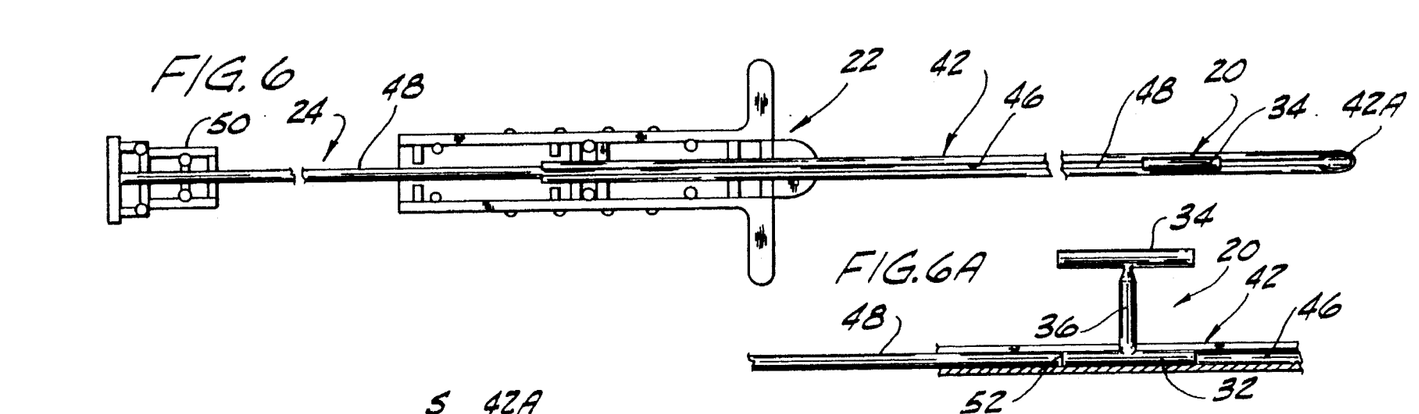
FIG. 6 is a plan of the system showing the push rod pushing the tack along the delivering instrument.
FIG. 6A is a fragmentary longitudinal section of the instrument with the push rod and tack therein.

The delivery instrument 22 has an elongated shaft, generally indicated at 42, having a sharp first end 42A and a second end 42B opposite the first end which is mounted on a handle 44. The elongated shaft 42 has a longitudinally extending channel 46 which is generally circular in cross section and opens longitudinally outwardly at the first end 42A and the second end 42B of the shaft. As shown in FIG. 6A, the channel 46 is sized and shaped to receive the first leg 32 of the tack 20 with the cross member 36 and second leg 34 of the tack projecting out of the channel. The first leg 32 may slide longitudinally in the channel 46, but is held from substantial movement in directions transverse to the lengthwise extension of the channel.

The push rod 24 includes a slender rod 48 which is generally circular in cross section and sized and shaped for sliding reception in the channel 36 through the opening at the second end 42B of the elongated shaft 42. A handle 50 is attached to the rod 48 at one end to facilitate holding and manipulation of the rod. As shown in FIGS. 6 and 6A, an opposite end 52 of the rod 48 is constructed for engagement with the tack 20 in the channel 46 for pushing the tack in the channel from the second end 42B to the first end 42A of the elongated shaft 42, thereby to place the tack in the meniscus M for closing the tear T.

The procedure for repairing a tear T in the meniscus M typically begins by introducing saline solution into the knee through a large bore needle which pierces the knee through a small incision known as a portal to increase the working area around the knee joint. Equipment (not shown) continuously flushes the knee joint with saline solution, which is pumped into the knee and then withdrawn by the equipment. A cannula (not shown) is inserted through a second portal for carrying an arthroscope (not shown) into the knee so that the surgeon may observe the interior of the knee, including particularly the torn meniscus M. These steps are well known by those skilled in the art for preparation of the knee for arthroscopic surgery. It is to be understood that the precise preparatory steps may vary from the aforementioned and still fall within the scope of the present invention.

A third portal is made in the knee and another cannula (not shown) inserted through which the guide pin 26 is inserted to the vicinity of the tear T in the meniscus with the aid of the arthroscope. The sharpened end 28 of the guide pin is used to penetrate the meniscus M adjacent a first side F of the tear T in the meniscus. The guide pin 26 is pushed through the meniscus M and exits on a second side S of the tear T thereby forming a passage through the meniscus having an entrance on the first side F of the tear and an exit on the second side of the tear. The guide pin 26 is now positioned substantially as schematically shown in FIG. 2. The surgeon will either manipulate the guide pin 26 to close the tear or use another surgical tool (not shown), inserted through another portal in the knee, to close the tear. The surgeon then observes the guide pin 26 in the meniscus M using the arthroscope and determines the appropriate size of the tack 20 needed to close the tear T using the graduations 30 on the guide pin.

Figures 3, 4:
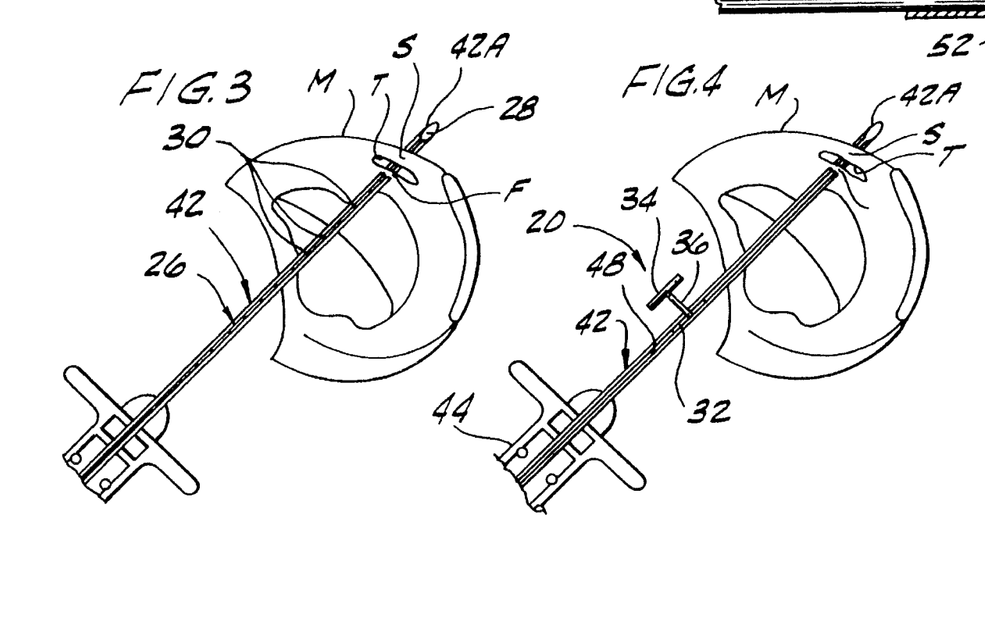

The guide pin 26 is now used to guide the delivery instrument 22 into position in the meniscus M. An unsharpened end 56 of the guide pin is received through the opening of the channel 36 in the first end 42A of the instrument 22 into the channel. The elongated shaft 42 is pushed down the guide pin 26 into the knee so that the first end 42A enters the passage formed in the meniscus M through its entrance on the first side F of the tear and leaves the passage through its exit on the second side S of the tear. The delivery instrument 22 is now generally in the position shown in FIG. 3 of the drawings. The guide pin 26 is withdrawn from the meniscus M and the knee through the opening in the channel 36 at the second end 42B of the elongated shaft, but the delivery instrument 22 stays in place substantially as shown in FIG. 4.

The surgeon has previously selected the appropriate size of tack 20 according to measurements made with the guide pin. The cross member 36 of the tack should be sufficiently short so that the first and second legs 32, 34, compress the meniscus enough to close the tear, but sufficiently long to allow the tack to be placed in the meniscus without damaging the meniscus tissue. Having selected the appropriately sized tack 20, the surgeon inserts the first leg 32 into the channel 46 through the opening at the second end 42B of the elongated shaft. The rod 48 of the push rod 24 is then telescopically received in the channel 46 through the opening at the second end 42B for pushing the first leg 32 of the tack down the channel thereby to deliver the tack to the tear T in the meniscus.

Upon reaching the first side F of the tear T in the meniscus M, the first leg 32 of the tack 20 passes through the entrance and into the passage in the meniscus (while remaining in the channel 46 of the delivery instrument 22). Initially, the second leg 34 and/or the cross member 36, which are disposed outside the channel 46, engage the meniscus M and are held from entering the passage. The obstruction provided by the meniscus M causes the cross member 36 and first leg 32 to resiliently flex relative to one another from their relaxed configuration to a configuration in which the cross member is nearly parallel to the lengthwise extension of the first leg. As the first leg 32 of the tack is pushed further through the passage toward its exit, the cross member 36 is drawn into the passage although it remains substantially outside the channel 46. The lengthwise extension of the second leg 34 is transverse to the lengthwise extension of the passage such that the second leg is adapted to engage the meniscus M around the entrance of the passage and will not enter the passage.

Figure 5:
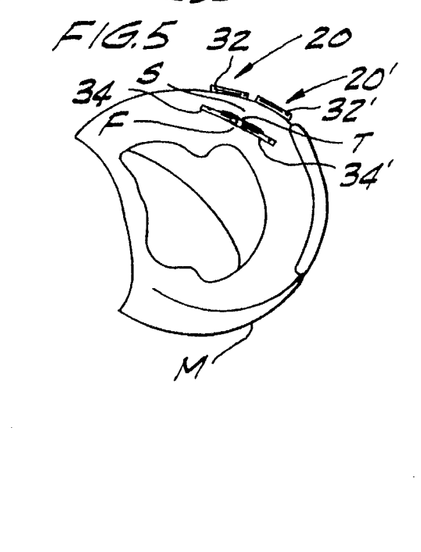

Eventually, the first leg 32 is pushed by the push rod 24 out of the passage and the channel 46 through the opening at the first end 42A of the elongated shaft 42, and the first leg moves back to its relaxed position relative to the cross member 36. In this position, the lengthwise extension of the first leg 32 is also transverse to the lengthwise extension of the passage so that the first leg is adapted to engage the meniscus M across the exit of the passage and cannot move back into the passage through the exit. The cross member 36 is disposed in the passage with its lengthwise extension parallel to that of the passage. The surgeon withdraws the delivery instrument 22 from the meniscus M and the knee, leaving the tack 20 in the position shown in FIG. 5. The first leg 32 and second leg engage and compress the meniscus M on the second side S and first side F of the tear T, respectively, to at least partially close the tear. If the tear T is sufficiently large a second tack 20' (shown in FIG. 6), having first and second legs 32' and 34', respectively, may have to be implanted in the meniscus M using substantially the same procedure as used for the first tack.

Once the appropriate number of tacks (e.g., tacks 20 and 20') have been placed in the meniscus M to properly close the tear T, the arthroscope is withdrawn and the portals made in the knee are sutured. The equipment (not shown) pumping saline solution into the knee joint is turned off and at least a portion of the saline is drained from the knee joint. The rest of the saline solution can be absorbed by the body. The patient is ready to begin recovery from the injury. As mentioned above, the tacks are made of material which is absorbable by the body so that, over time, they dissolve leaving only the repaired meniscus M.

The generally principles of the foregoing method are equally applicable for closing openings in soft tissue elsewhere in the body besides the knee joint. For instance, the system and method lend themselves to repairing intra-abdominal incisions made during laprascopic surgery. Presently, surgeons use the laparoscope in procedures to remove the gall bladder, appendix and other lesions within the abdominal cavity. The incisions made in soft tissue inside the body in this type of surgery could be closed using the system and method described above.

Figure 7:
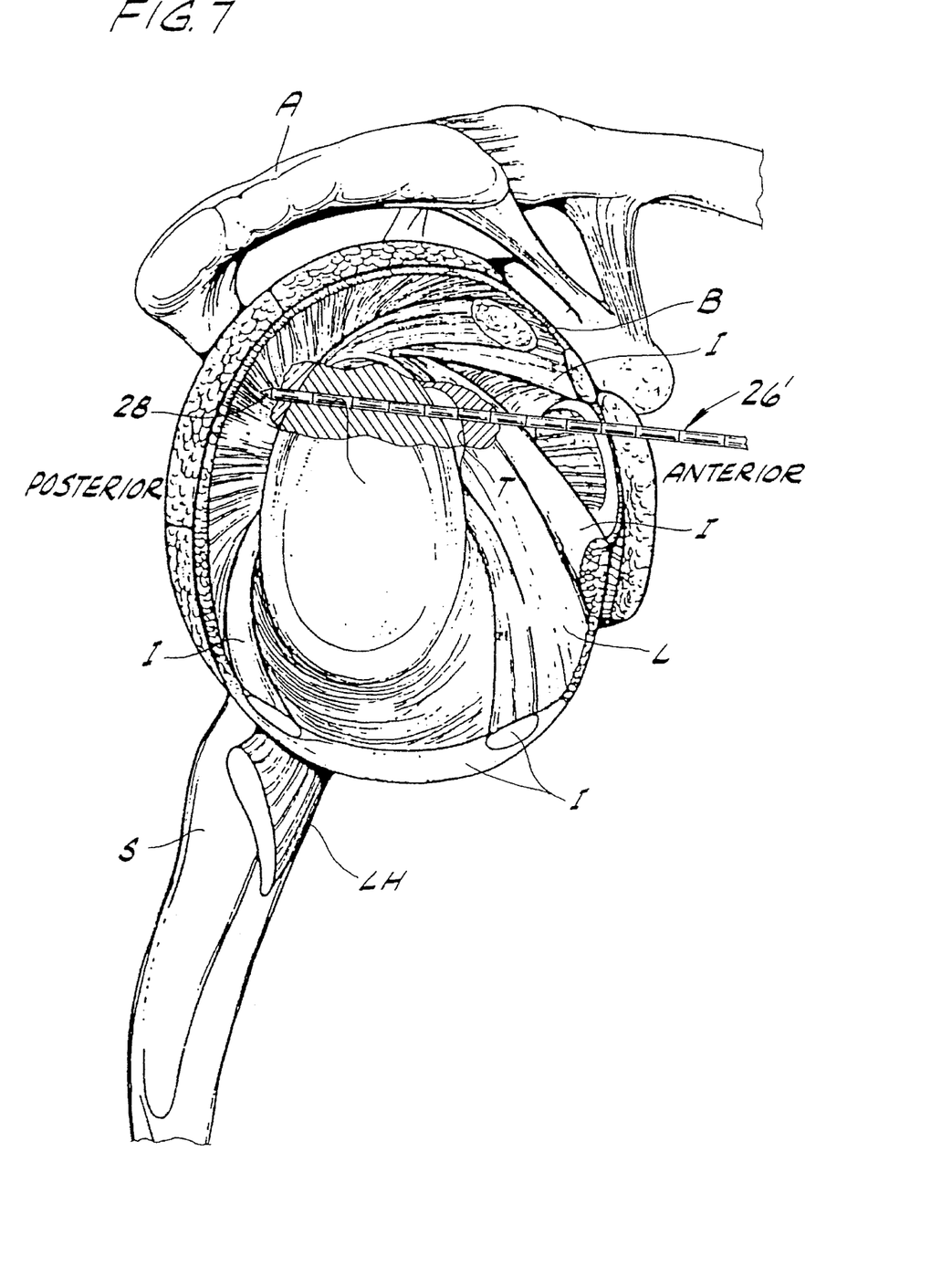
FIGS. 7–9 are a side elevation of a shoulder joint with the humerus removed and illustrating a repair of a tear of the glenoid labrum.
Figure 8:
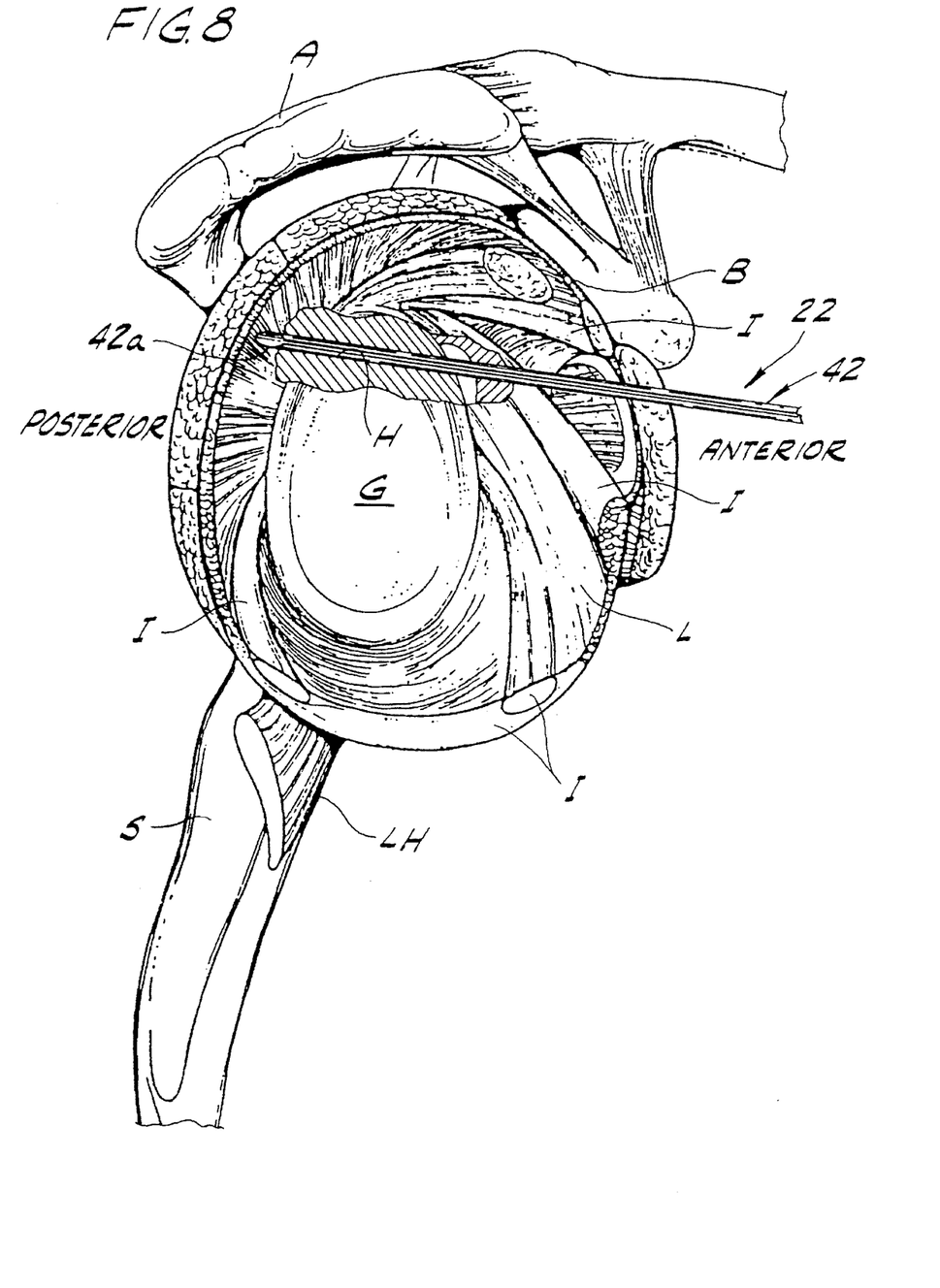
Figure 9:
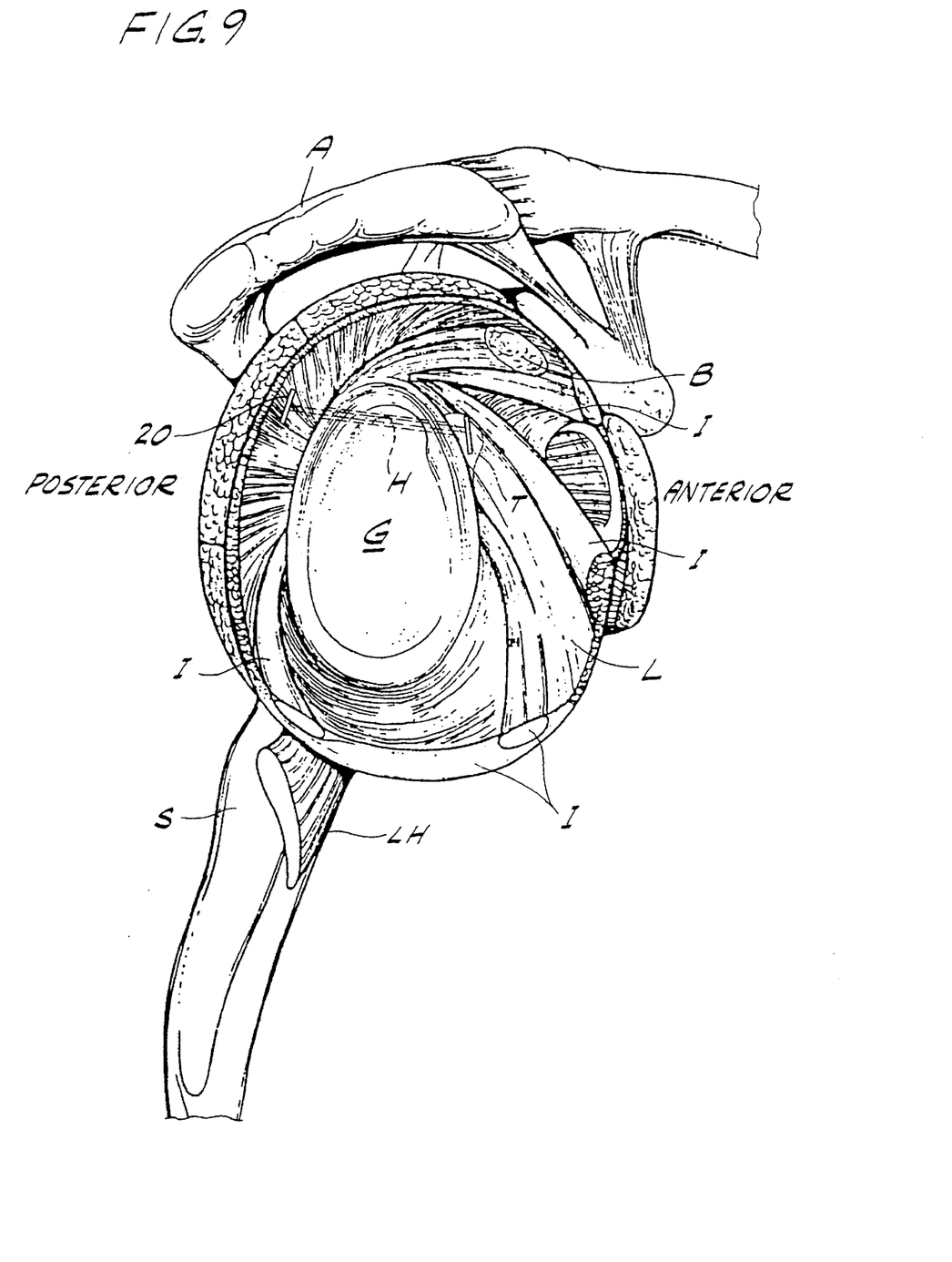

Referring now to FIGS. 7–9 of the drawings, another example of arthroscopic surgery which could be carried out using the principles of the present invention is repair of tears in the glenoid labrum in the shoulder joint. A portion of the shoulder blade S and the acromium A are illustrated, as well as portions of the glenohumeral ligaments I, biceps B and long head LH of the triceps muscle. FIGS. 7–9 depict the repair of a tear T of the glenoid labrum L in which the labrum was torn away from the glenoid G along an anterior edge of the glenoid. The tear T, which has already been closed as shown in FIG. 9, is illustrated in phantom. However, tears (not shown) in the glenoid labrum spaced away from the glenoid could also be repaired. Such a procedure would be substantially the same as repairing the meniscus because no bone is involved in repairing the tear.

The shoulder joint is enlarged by pumping a saline solution into the joint as done for the knee in preparation of repairing the meniscus. The procedure for repairing the tear T in the glenoid labrum L may be carried out by making a posterior portal adjacent to the shoulder joint and introducing the arthroscope through the portal into the joint. An examination of the joint is conducted to locate the tear T, and a pin (such as guide pin 26) is inserted through the portal, and out the anterior side of the shoulder joint to locate an anterior portal directly opposite the posterior portal. If the tear is old, it will be necessary to remove scar tissue around the tear such as by inserting a curved curette (not shown) to scratch the labrum L and glenoid G to freshen the tear and bone. The use of the curette is well known to those of ordinary skill in arthroscopic surgery.

A canula (not shown) is inserted through the anterior portal to the vicinity of the tear T to be repaired. A hardened pin 26' (e.g., a Steinmann pin) is inserted through the canula and pushed through the soft tissue of the labrum L from the first side of the tear T to and against the bone of the edge of the glenoid G which would be the second side of the tear. The pin 26' is substantially similar to the guide pin 26 (including the graduations 30 for sizing the tack 20), but has a hardened tip. The pin 26' is rotated by a surgical drill (not shown) to drill a hole H through the bone deep to the articular surface of the glenoid located in the neck of the scapula (FIG. 7). The hole H exits the neck of the scapula on its posterior surface. Frequently it will be necessary to drill several holes through the scapular neck, one for each tack 20 needed to close the tear T. The pin extends through the labrum L from a first side of the tear T, through the hole H which begins on the second side of the tear at the edge of the glenoid G and continues through the scapular neck deep to the cartilaginous articular surface of the glenoid and exits on the posterior surface of the scapular neck.

The hardened pin 26' and canula are then removed and instrument 22 is inserted through the anterior portal, through the labrum L opposite the hole H drilled in the scapular neck and into the hole. On the posterior side of the scapular neck, the instrument 22 exits the hole H and passes a short way into the labrum L on the opposite side of the scapular neck from the tear T (see FIG. 8). In this embodiment, the passage referred to in the claims extends through the bone. A tack 20 is delivered in the instrument 22 to the tear in the same way as described above for repair of the meniscus. The leg 34 of the tack 20 outside of the channel 46 engages the labrum L anteriorly of the tear T and is held from movement into the passage in the labrum. The other leg 32 and cross member 36 pass into the labrum L and the hole H and through the scapular neck G. The leg 32 exits the channel 46 of the instrument 22 on the posterior side of the scapular neck and moves to a position crosswise to the passage, thereby preventing withdrawal of the leg back into the hole H. The cross member 36 has been sized so that the portion of the labrum L on the anterior side of the tear engaged by the leg 34 is pulled into engagement with the bone, closing the tear T and permitting the labrum to heal and rejoin the glenoid G (see FIG. 9). The process is repeated as many times as necessary to insert all of the tacks 20 needed to close the tear.

In view of the above, it may be seen that the several objects and features of the present invention are achieved and other advantageous results are attained.

As various changes could be made in the above constructions without departing from the scope of the invention, it is intended that all matter contained in the above description or shown in the accompanying drawings shall be interpreted as illustrative and not in a limiting sense.

What is claimed is:

1. A method for closing an opening in soft tissue inside the body, the method comprising the steps of:

making an incision in the body for permitting access to the interior of the body generally adjacent to the location of the opening in the soft tissue inside the body;

inserting an instrument through the incision to the vicinity of the opening in the soft tissue inside the body;

passing the instrument through the soft tissue and across the opening in the soft tissue generally from a first side of the opening to a second side of the opening opposite the first side, a portion of the instrument lying in a passage having an entrance on the first side of the opening and an exit on the second side of the opening;

delivering said suture means in the instrument to said passage, said suture means comprising a first leg, a second leg spaced from the first leg and a cross member extending generally transversely with respect to the lengthwise extension of the first and second legs and connecting the first and second legs;

pushing the first leg and cross member generally lengthwise into said passage through the entrance thereof with the first leg and the cross member being resiliently deflected from their relaxed positions relative to one another, the first leg moving back to its relaxed position relative to the cross member upon passing out of said passage through the exit thereof and leaving the instrument, the first leg thereafter extending transversely with respect to the lengthwise extension of said passage across the exit thereof so that the first leg cannot move back into said passage through the exit, the second leg extending generally transversely with respect to the lengthwise extension of said passage across the entrance thereof so that the second leg cannot move into said passage through the entrance, and the cross member being disposed in said passage;

the cross member having a length less than the length of said passage such that said suture means compresses the soft tissue to at least partially close the opening.

2. A method as set forth in claim 1 wherein the instrument has an elongated channel therein opening at the end of the instrument which enters the soft tissue and at an opposite end of the instrument located outside the body, the channel being shaped and dimensioned for receiving the first leg of said suture means therein with the lengthwise extension of the first leg parallel to the lengthwise extension of the channel, and wherein the step of pushing the first leg and cross member comprises the steps of:

inserting the first leg of said suture means into the channel in the instrument with the leg being held from substantial radial movement in the channel;

inserting an end of a push rod into the channel from the end of the instrument outside the body and engaging the first leg therewith;

sliding the push rod into the channel thereby pushing the first leg in the channel, through said passage in the soft tissue and out of the channel at the end of the instrument which enters the soft tissue; and withdrawing the instrument from the soft tissue with said suture means remaining in the soft tissue to close the opening therein.

3. A method as set forth in claim 2 further comprising, prior to the steps of inserting the instrument through the incision, the steps of:

inserting elongated guide pin means through the incision to the vicinity of the opening in the soft tissue;

passing the end of said guide pin means through the soft tissue and across the opening in the soft tissue generally from one of the first and second sides to the other of the first and second sides of the opening thereby to form said passage;

and wherein the step of inserting the instrument through the incision, and passing through said passage comprise the steps of, sliding the instrument over said guide pin means at an end of said guide pin means opposite the end which passes through the soft tissue with said guide pin means being received in the channel of the instrument, pushing the instrument along said guide pin means toward the end of said guide pin means which passes through the soft tissue, the end of the instrument entering said passage in the soft tissue through its entrance and exiting said passage through the exit, and wherein the method further comprises the step of withdrawing said guide pin means from the instrument and the body through the opening in the channel at the end of the instrument outside the body.

4. A method as set forth in claim 3 wherein the method further comprises the step, prior to said step of withdrawing said guide pin means from the instrument, of gauging the proper size of suture means needed to close the opening using longitudinally spaced graduations on said guide pin means.

5. A method as set forth in claim 1 wherein said guide pin means has longitudinally spaced graduations thereon, and wherein the method further comprises, prior to the steps of inserting the instrument through the incision, the steps of:

inserting elongated guide pin means through the incision to the vicinity of the opening in the soft tissue;

passing the end of said guide pin means through the soft tissue and across the opening in the soft tissue generally from one of the first and second sides to the other of the first and second sides of the opening thereby to form said passage, closing the opening;

gauging the size of suture means needed to close the opening using the graduations on said guide pin.

6. A method for closing an opening formed by separation of soft tissue from a bone with the bone being located generally at one of a first side and a second side of the opening, the method comprising the steps of:

making an incision in the body for permitting access to the interior of the body generally adjacent to the location of the opening between the bone and soft tissue inside the body;

inserting an elongated pin through the incision to the bone in the vicinity of the opening;

drilling a hole through the bone, the hole having a first end generally at the opening and a second end spaced from the opening;

inserting an instrument through the incision to the vicinity of the opening inside the body;

passing the instrument generally from the first side of the opening to the second side of the opening opposite the first side such that a portion of the instrument lies in a passage defined in part by the hole in the bone and further including a portion in the soft tissue, the passage having an entrance and an exit on opposite sides of the opening from each other;

delivering suture means in the instrument to said passage, said suture means comprising a first leg, a second leg spaced form the first leg and a cross member extending generally transversely with respect to the lengthwise extension of the first and second legs in a relaxed position of said suture means, the cross member connecting the first and second legs;

pushing the first leg and cross member generally lengthwise into said passage through the entrance thereof with the first leg and the cross member being resiliently deflected from their relaxed positions relative to one another, the first leg moving back to its relaxed position relative to the cross member upon passing out of said passage through the exit thereof and leaving the instrument, the first leg thereafter extending transversely with respect to the lengthwise extension of said passage across the exit thereof so that the first leg cannot move back into said passage through the exit, the second leg extending generally transversely with respect to the lengthwise extension of said passage across the entrance thereof so that the second leg cannot move into said passage through the entrance, and the cross member being disposed in said passage, one of the first and second legs of said suture means being located outside the second end of the hole in the bone;

cross member having a length less than the length of said passage such that said suture means compresses the soft tissue against the bone to at least partially close the opening.

7. A method as set forth in claim 6 wherein the instrument has an elongated channel therein opening at the end of the instrument which enters the passage and at an opposite end of the instrument located outside the body, the channel being shaped and dimensioned for receiving the first leg of said suture means therein with the lengthwise extension of the first leg parallel to the lengthwise extension of the channel, and wherein the step of pushing the first leg and cross member comprises the steps of:

- inserting the first leg of said suture means into the channel in the instrument with the leg being held from substantial radial movement in the channel;
- inserting an end of a push rod into the channel from the end of the instrument outside the body and engaging the first leg therewith;
- sliding the push rod into the channel thereby pushing the first leg in the channel, through said passage and out of the channel at the end of the instrument which enters the passage; and
- withdrawing the instrument from the passage with said suture means remaining in the bone and soft tissue to close the opening therein.

* * * * *

UNITED STATES PATENT AND TRADEMARK OFFICE
CERTIFICATE OF CORRECTION

PATENT NO. : 5,467,786

DATED : November 21, 1995

INVENTOR(S) : William C. Allen et al.

It is certified that error appears in the above-identified patent and that said Letters Patent is hereby corrected as shown below:

In the title on the cover page, item [54] and Col, 1, line 2, "Reparing" should read ---Repairing---.

Column 8, claim 6, line 47, "instrument generally" should read ---instrument across the opening generally---.

Column 8, claim 6, line 56, "spaced form" should read ---spaced from---.

Signed and Sealed this

Twenty-eighth Day of May, 1996

Attest:

BRUCE LEHMAN

Attesting Officer     Commissioner of Patents and Trademarks